United States Patent [19]

Kuzuya et al.

[11] Patent Number: 5,306,505
[45] Date of Patent: Apr. 26, 1994

[54] PLASMA-IRRADIATED SOLID PREPARATION

[75] Inventors: Masayuki Kuzuya, Gifu; Sumio Watanabe, Ibaraki, both of Japan

[73] Assignee: Eisai Co., Ltd., Tokyo, Japan

[21] Appl. No.: 678,330

[22] PCT Filed: Dec. 12, 1990

[86] PCT No.: PCT/JP90/01625
§ 371 Date: Apr. 22, 1991
§ 102(e) Date: Apr. 22, 1991

[87] PCT Pub. No.: WO91/08736
PCT Pub. Date: Jun. 27, 1991

[30] Foreign Application Priority Data

Dec. 12, 1989 [JP] Japan .................. 1-322881
Nov. 26, 1990 [JP] Japan .................. 2-322071

[51] Int. Cl.$^5$ .................................. A61K 9/20
[52] U.S. Cl. ........................... 424/464; 424/472; 424/497
[58] Field of Search .................. 424/464, 497, 472

[56] References Cited

U.S. PATENT DOCUMENTS 4,652,441 3/1987 Okada .................. 424/497
5,008,113 4/1991 Kokubo ................ 424/464
5,024,842 6/1991 Edgren ................. 424/472

OTHER PUBLICATIONS

Patent Abstracts of Japan, vol. 8, No. 52, C-213 (1489), Mar. 9, 1984.
Chemical Abstracts, vol. 113, No. 2, Jul. 9, 1990, Abstract No. 11975, "Solid crosslinking of plasma irradiated polymer powder and its application to drug delivery systems".
Chemical Abstracts, vol. 111, No. 4, Jul. 24, 1989, Abstract No. 24065, "Nature of free radical formation in acrylic resins by plasma-irradiation".

Primary Examiner—Thurman K. Page
Assistant Examiner—William E. Benston, Jr.
Attorney, Agent, or Firm—Flynn, Thiel, Boutell & Tanis

[57] ABSTRACT

By forming a multi-layer preparation comprising a tablet or granule containing a medicine as the core and the outermost layer comprising a plasma-decomposable polymer and a plasma-crosslinkable polymer and irradiating the outermost layer with a plasma about release-regulating preparations according to the plasma irradiation, the direct exposure of the medicine to the plasma can be avoided and the release pattern can be controlled more easily.

12 Claims, 16 Drawing Sheets

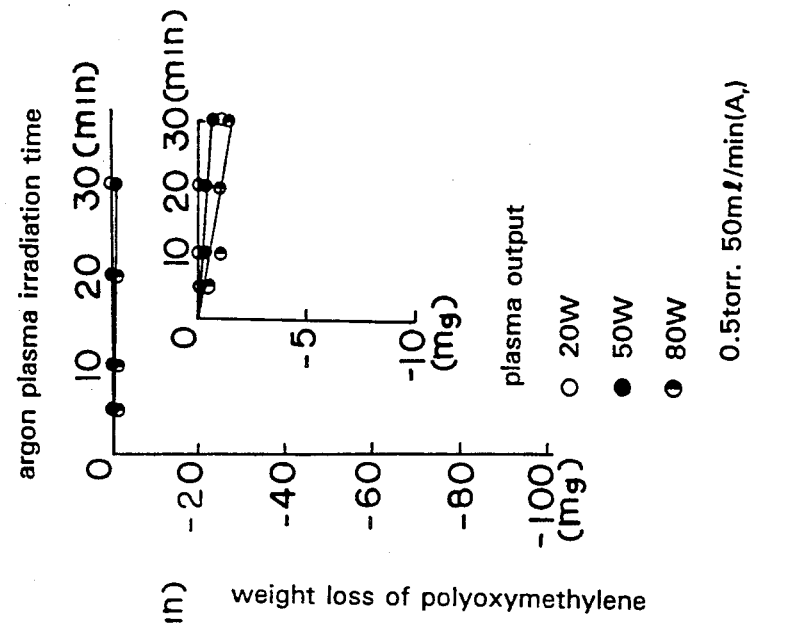
FIG. 6c
FIG. 6b
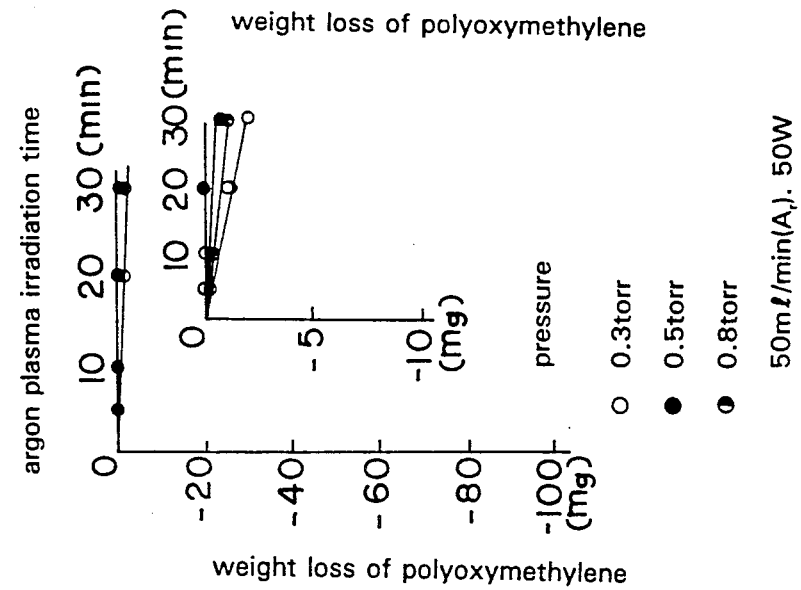
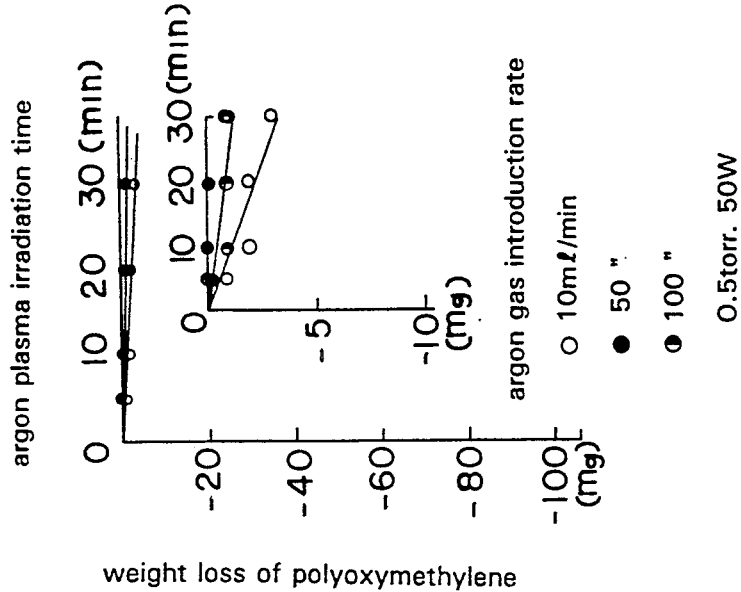
FIG. 6a

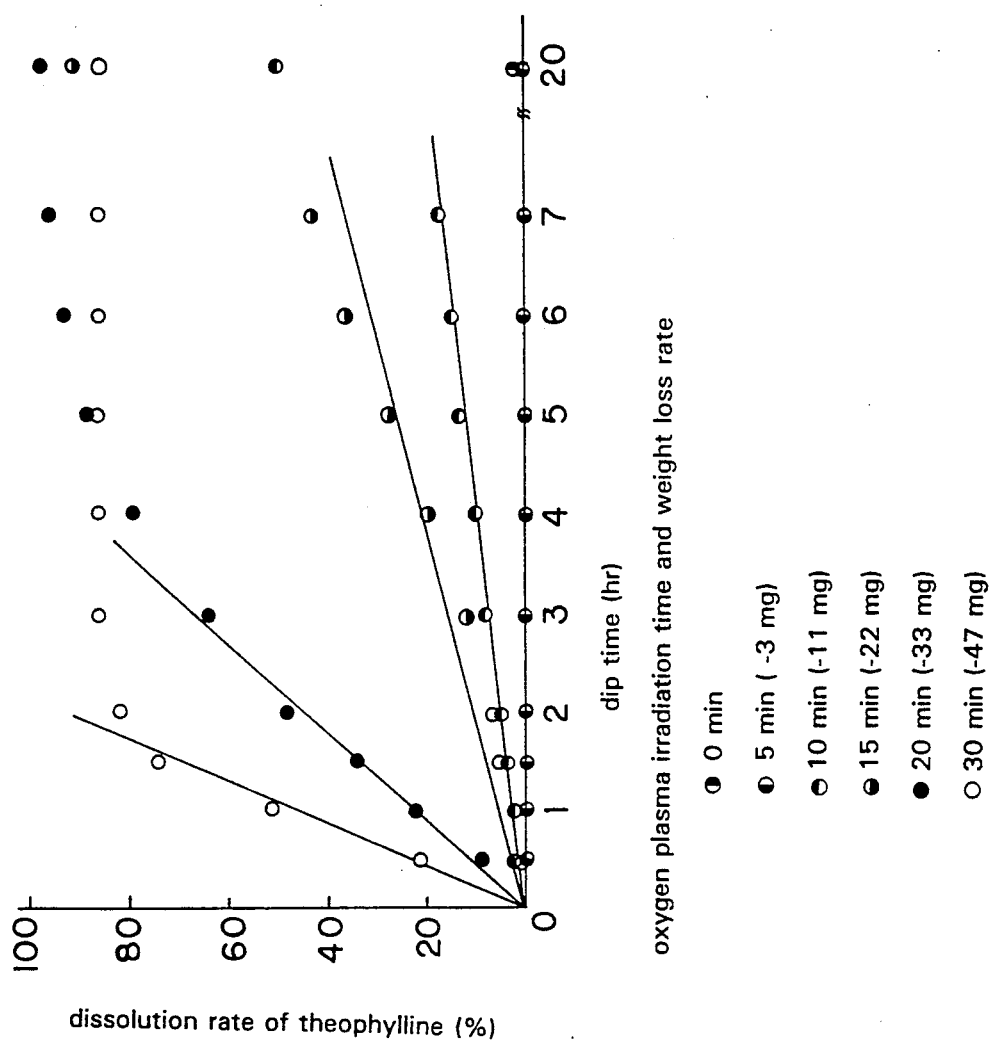

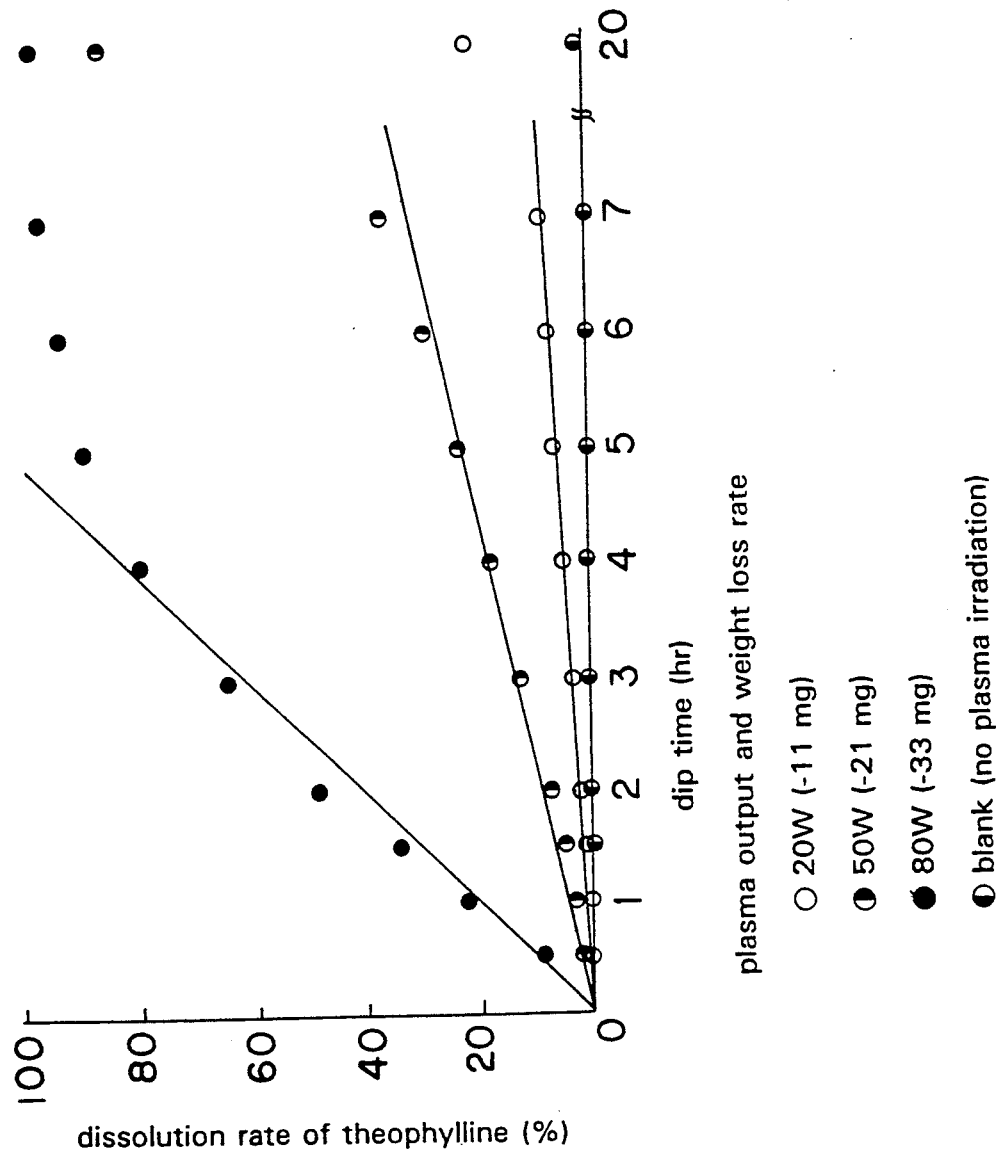

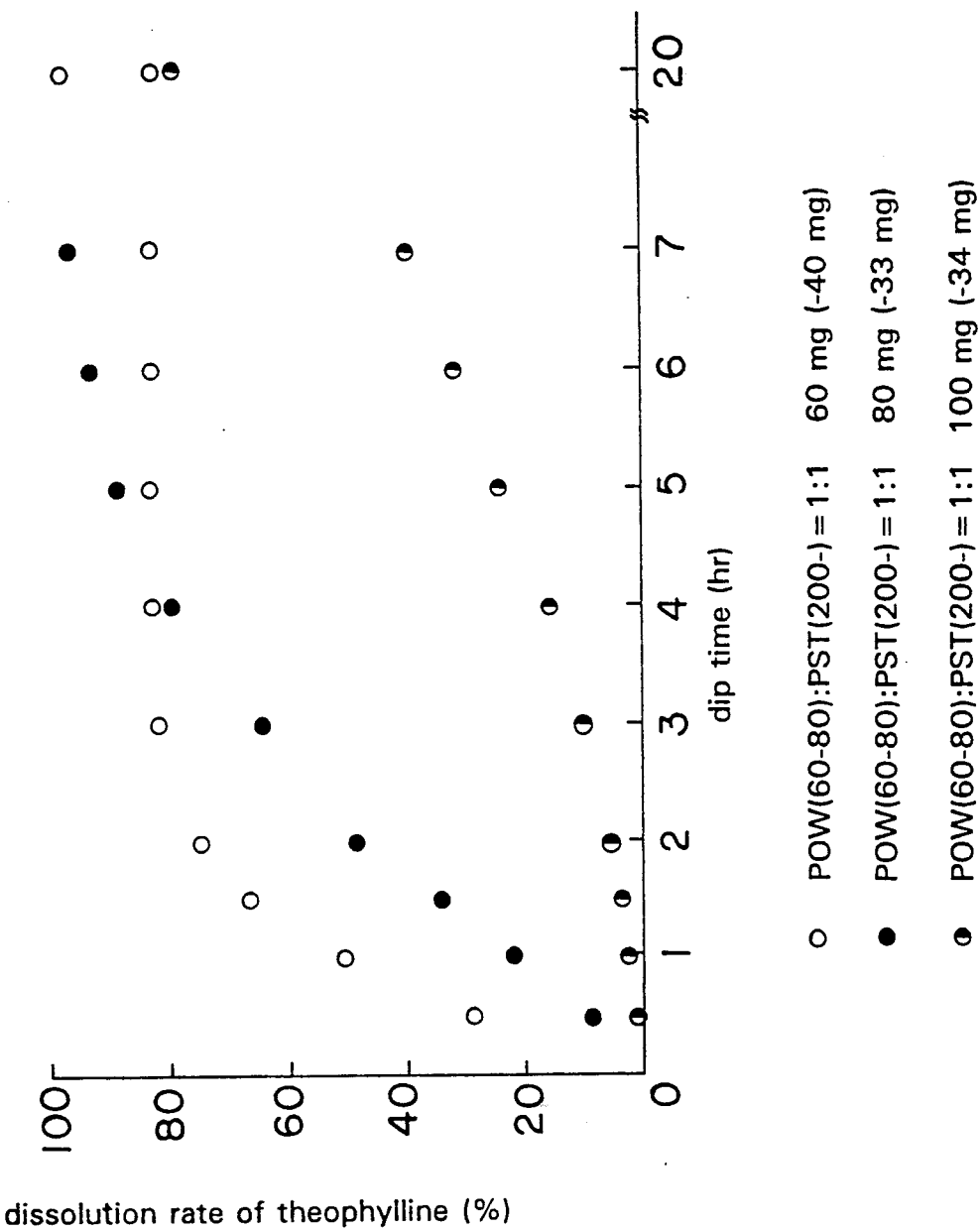

oxygen plasma irradiation and weight loss rate

○  1.0hr  <- 8mg>
●  2.0hr  <-14mg>
◐  2.5hr  <-19mg>
◐  3.0hr  <-22mg> total weight of outer layer polymers and weight loss rate

◐ 60mg  <-15mg> → blank ◨

◑ 70mg  <-14mg> → blank ◨

● 80mg  <-14mg> → blank ■

○ 100mg <-16mg> → blank □ weight ratio of outer layer polymers and weight loss rate

● POM:PLA = 1:3  <-14mg> → blank  ■

○ POM:PLA = 1:1  <-24mg> → blank  □

◐ POM:PLA = 3:1  <-34mg> → blank  ◨

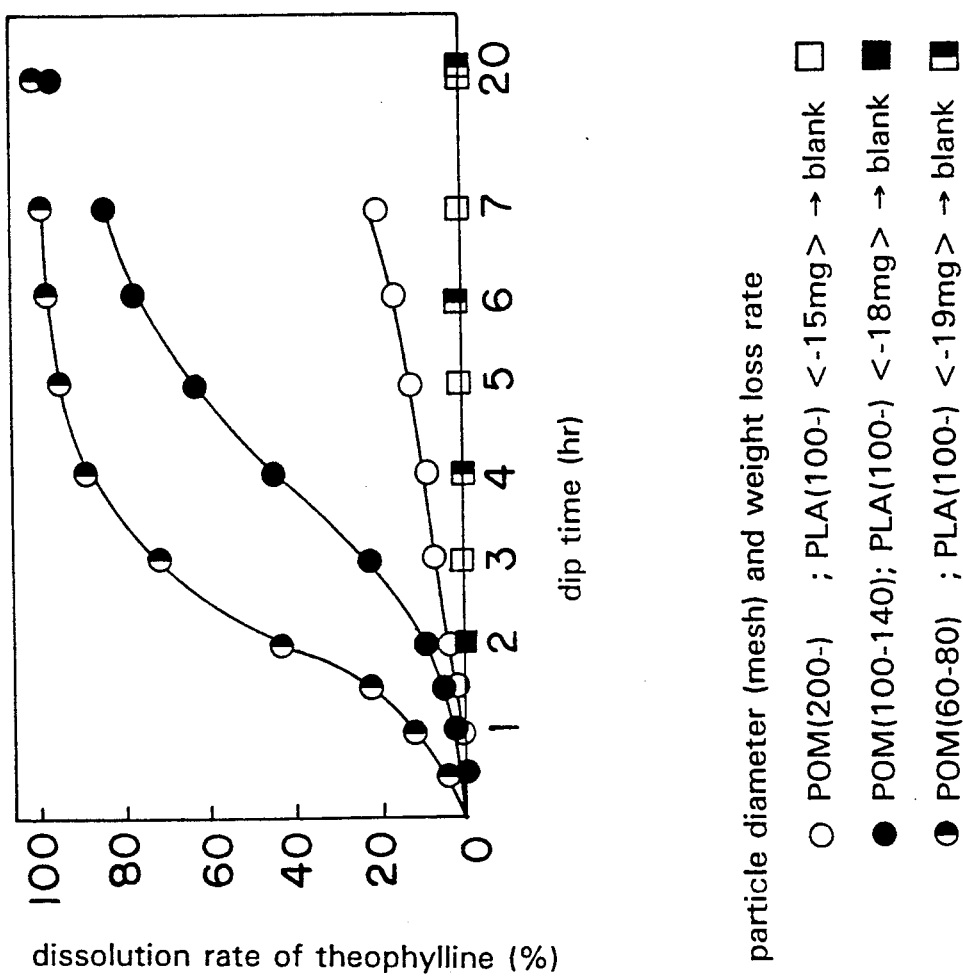

PLASMA-IRRADIATED SOLID PREPARATION

BACKGROUND OF THE INVENTION

1. Field of the Invention

The present invention relates to a solid preparation having a purpose and function of regulating the rate of releasing a medicine administered mainly orally in the digestive tracts and a process for producing it. In particular, the present invention relates to a multi-layer solid preparation characterized by having an outer layer comprising a plasma-decomposable polymer and a plasma-crosslinkable polymer and irradiated with a plasma for the above-described purpose and for obtaining the above-described function, and a process for producing it.

2. Description of the Prior Art

The matrix method is a method of designing a preparation having a purpose and function of regulating the rate of releasing a medicine in the digestive tracts. It is known to use a water-insoluble substance such as a wax or ethylcellulose as the material of the matrix. The matrix method is characterized by a mesh structure comprising a skeleton of a water-insoluble substance such as a wax or ethylcellulose. The rate of releasing the medicine from the mesh structure upon contact with the fluid in the digestive tracts is regulated by varying the properties of this structure.

The release of a medicine from the mesh structure depends mainly on a difference in the osmotic pressure between the inside and outside of the structure or, in other words, difference in the concentration of the medicine between them. Since the difference in concentration does not change for a considerably long time in the mesh structure, there is a tendency toward a zero-order release rate. Therefore, when a zero-order release rate was desired, a matrix-type preparation was frequently used heretofore. As the rate constant of the zero-order release varies depending on the size of the openings of the mesh and their uniformity, it is important to select the most suitable technique and contrivance for forming the openings of the mesh. Various techniques were developed for this purpose. They include a technique wherein a medicine-containing solid preparation is irradiated with γ-rays to form a mesh structure and a technique wherein the medicine-containing solid preparation is coated with a film comprising a water-soluble substance such as a sugar so that the water-soluble substance is eluted to form the mesh structure after the administration thereof. However, these methods still have problems. Namely, in the γ-ray irradiation method, the medicine is decomposed and deactivated and in the latter method, the coating film containing the water-soluble substance will be affected by the conditions in the digestive tracts.

The inventors have made intensive investigations for the purpose of developing a new functional material by a plasma reaction and, more particularly, for the purpose of developing a new drug delivery system with a plasma-irradiated polymer powder. The following references 1), 2) and 3) written by the inventors are to be referred to in the present invention:

1) Bulletin of the Gifu College of Pharmacy, Vol. 36 (1987), pp. 11 to 25, Masayuki KUZUYA New Plasma-started Polymerization,
2) "Chemical Engineering" published by Kagaku Kogyo-Sha in 1989, pp. 664 to 671; Masayuki KUZUYA, New DDS with Plasma-irradiated Polymer Powder, and
3) "Hyomen" published by Koshin-Sha in 1989, pp. 885 to 892.

It is well known that when an acrylic resin such as polymethyl methacrylate is subjected to radical irradiation, radicals are formed on the resin surface. The inventors have found that when a plasma-irradiated acrylic resin is tableted as indicated in References 2) and 3), the radicals on the resin surface cause crosslinking between the solids due to the compression in the tableting operation to form macro-matrix tablets. Namely the inventors succeeded in forming a matrix having a mesh structure regulated at will by suitably selecting the irradiation polymerization conditions and tableting compression conditions, unlike known matrixes. The Reference 2) discloses a case wherein theophylline is incorporated into an acrylic resin powder irradiated with an argon plasma and tableted and the behavior of theophylline eluted therefrom is investigated. It is described therein that the mesh structure of the matrix can be regulated at will by suitably selecting the irradiation polymerization conditions and tableting compression conditions and that, as a result, the diffusion and elution of theophylline as the rate-determining step can be controlled.

Thereafter the inventors proposed various matrix-type release-regulating preparations according to the plasma irradiation and investigated them. The inventors thus found that by forming a multi-layer preparation comprising a tablet or granule containing a medicine as the core and the outermost layer comprising a plasma-decomposable polymer and a plasma-crosslinkable polymer and irradiating the outermost layer with a plasma, the direct exposure of the medicine to the plasma can be avoided and the release pattern can be controlled more easily. The present invention has been completed after further investigations made on the basis of this finding.

The present invention provides a multi-layer solid preparation characterized by having an outer layer comprising a plasma-decomposable polymer and a plasma-crosslinkable polymer and irradiated with a plasma. The present invention provides also a process for producing a multi-layer solid preparation characterized by forming an outermost layer comprising a plasma-decomposable polymer and a plasma-crosslinkable polymer and then irradiating the layer with a plasma.

BRIEF DESCRIPTION OF THE DRAWINGS

FIGS. 6(a), 6(b) and 6(c) show the results of the experiments on the dependency of the rate of weight loss of polystyrene on the argon gas introduction rate, pressure or plasma output obtained when argon gas was introduced. FIGS. 3(a) through FIG. 6(a) show the relationship between the gas introduction rate and weight loss rate, FIG. 3(b) through FIG. 6b) show that between the pressure and weight loss rate, FIG. 3(c) through FIG. 6(c) show that between the plasma output and weight loss rate. FIG. 7 shows the relationship between the oxygen plasma irradiation time and dissolution rate of theophylline. FIG. 8 shows the relationship between the oxygen plasma irradiation output and dissolution rate of the theophylline. FIG. 9 shows the relationship between the ratio of the total weight of the polymers forming the outer layer to the active ingredient (theophylline) and dissolution rate of theophylline. FIG. 17 shows the relationship between the combination of polymers having various particle diameters in the outer layer and dissolution rate of theophylline.

In FIGS. 1 and 2, the reference numbers identify parts as follows:

Figure 1:
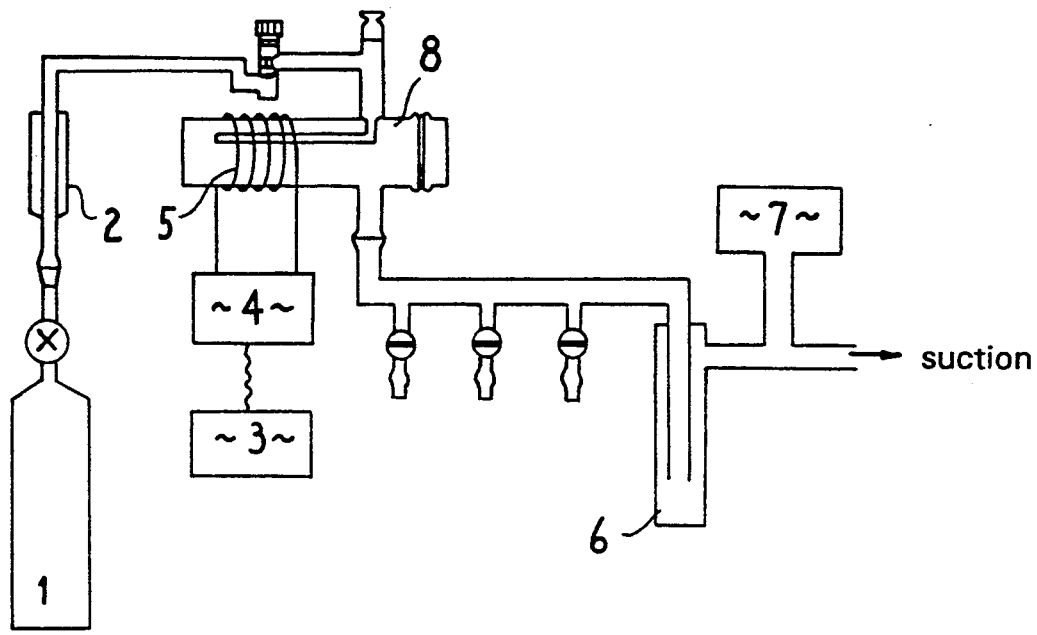
FIG. 1 is a schematic drawing of the apparatus used for the production of the multi-layer solid preparation of the present invention.

1: gas cylinder, 2: flow meter, 3: high-frequency generating power source, 4: matching network, 5: high-frequency coil, 6: trap, 7: pressure gauge, 8: reactor, 9: tablet, 10: glass sample holder, 11: O-ring.

A detailed description will now be made on the present invention.

In the present invention, the term "plasma-decomposable polymer" refers to a polymer which forms a radical due to the breakage of the polymer main chain upon irradiation with an inert plasma (such as an inert gas) to reduce its weight to a large extent. Examples of them include polymers of the general formula:

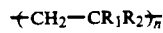

wherein $R_1$ and $R_2$ each represent a monovalent organic compound, produced from 1,1-disubstituted vinyl monomers, such as polyisobutylene, poly-α-methylstyrene, polymethacrylic acid, polymethyl methacrylate or polymethacrylamide. Since oxygen is quite easily split off during the plasma irradiation, polymers having an ether bond in the main chain, such as polyoxymethylene and polysaccharides (for example, celluloses), are also typical plasma-decomposable polymers.

The term "plasma-crosslinkable polymer" herein refers to a polymer which forms a radical of a polymer main chain type upon irradiation with a plasma to conduct the surface crosslinking reaction and thereby to cause only a slight weight loss. Examples of them include polyethylene and polymers of the general formula:

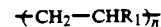

wherein $R_1$ represents a monovalent organic compound, produced from 1-substituted vinyl monomers, such as polypropylene, polystyrene, polyacrylic acid, polymethyl acrylate, polyacrylamide or polylactic acid.

Practically, however, not only one reaction proceeds exclusively but both decomposition and crosslinking reactions proceed upon irradiation with a plasma. Thus the reactions are classified according to the main reaction. For instance, hydrocarbon polymers such as polypropylene are classified into the plasma-crosslinkable polymers. When they are irradiated with an inert gas plasma to form a polyenyl radical (radical having many double bonds conjugated with one another) on the polymer main chain, they are not decomposed as such. However, when they are irradiated with an oxygen plasma, oxygen atoms in the plasma react to accelerate the oxidative destruction reaction to break the main chain. This is called a "plasma-decomposable polymer". Although the plasma-decomposable polymer and plasma-crosslinkable polymer can thus be broadly classified into the two groups in the present invention, the polymers are not limited to those described above. Namely, one of the two polymers used as the components undergoes mainly the decomposition reaction and the other undergoes mainly the crosslinking reaction upon plasma irradiation. The former is called the plasma-decomposable polymer and the latter is called the plasma-crosslinkable polymer.

Commercially available polymers can be used as the plasma-decomposable polymer and the plasms-crosslinkable polymer. If necessary, they can be purified, pulverized and sieved to obtain particles having a desired uniform diameter. Further, the polymers synthesized and then treated in the same manner can also be used.

When the temperature of a substance is gradually elevated, it changes from a solid to a liquid and then to a gas. When a high energy is further applied to the gas, it is dissociated into particles having a negative charge and those having a positive charge. The plasma is more highly excited than an ordinary gas and is unstable. The ionized gas can be broadly classified into hot (high-temperature) plasma and low-temperature plasma according to its state. All the particles in the former have a high kinetic energy and are in a thermal equilibrium state and, therefore, the former is called "equilibrium plasma". In the latter, only a part of the electrons in the gas have a high level of energy and is dissociated like a low-pressure ionized gas. Most of the components are molecules (neutral radicals and ions) and electrons and are not in a thermal equilbrrium state and, therefore, they are called "non-equilibrium plasma", which is used as a chemical plasma. In the irradiation with an inert element plasma such as argon or helium plasma, the ultraviolet rays and particles that are irradiated play the main roles in terms of the effect. They are effective in modifying or etching the surface of an object. On the other hand, molecular plasmas of oxygen, nitrogen, etc., are employed for the surface modification, since the respective atomic groups are introduced into the surface of the object.

Any low-temperature plasma other than an organic gas plasma is usable in the present invention. Inert gas plasmas such as argon and helium plasmas, and plasmas of oxygen, nitrogen, hydrogen and even water and air are usable. The plasmas of oxygen and air are particularly suitable, since they accelerate the oxidative destruction reaction of the plasma-decomposable polymer to accelerate the decomposition thereof. The use of the plasma of air is most desirable from the viewpoints of the reaction and economization. However, the plasmas are not limited to them but any low-temperature plasma other than organic gases is usable in the present invention.

A series of discharge techniques is usually employed for forming a plasma. In plasma chemisty, it is possible to entirely remove the electrodes from the discharge region and a high-frequency, non-polar discharge at 13.56 MHz or 27.12 MHz, the use of which for medical and industrial purpose is known is employed. An inductive coupling system wherein a coil is used or a capacitive coupling system wherein an electrode plate (a capacitor) is used can be employed for charging in such a non-polar discharge system is which a necessary energy is supplied from the outside of the reaction vessel. Various reaction vessels and apparatuses can be used therefor.

Figure 2:
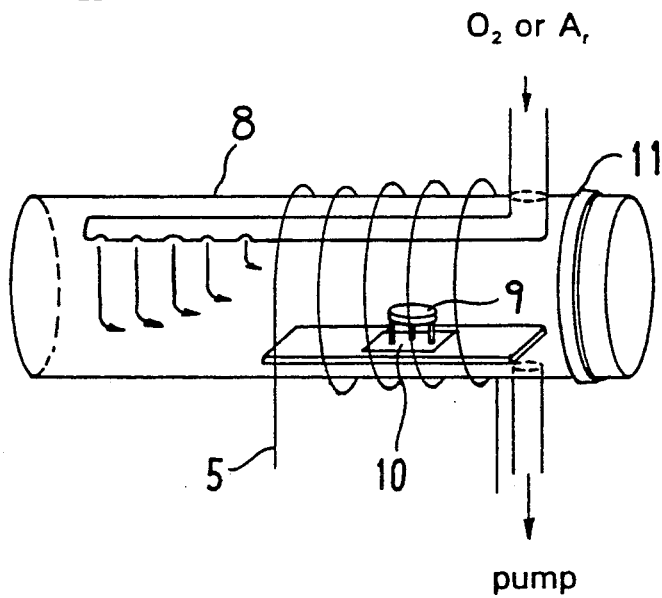
FIG. 2 is an enlarged view of the reactor of the apparatus.
Figure 3C:
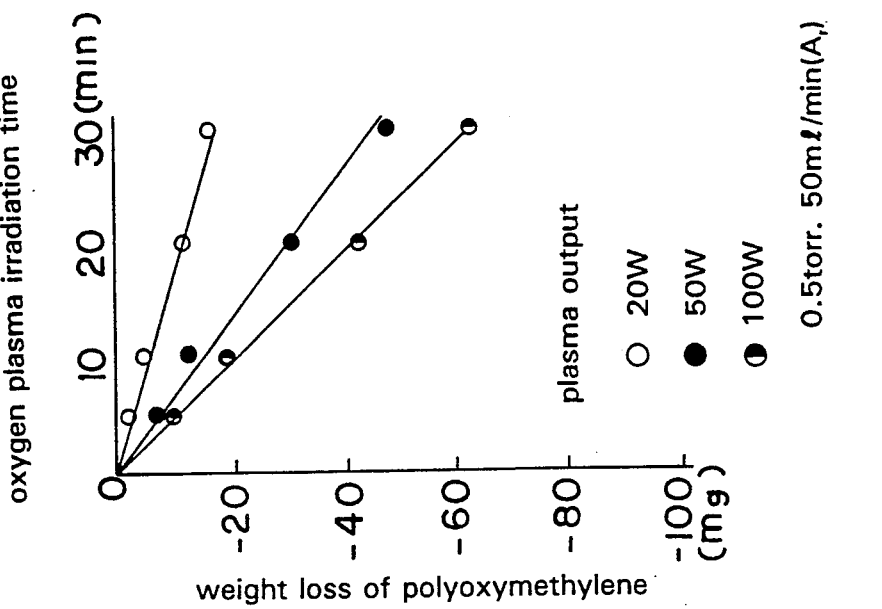
FIGS. 3(a), 3(b) and 3(c) show the results of the experiments on the dependency of the rate of weight loss of polyoxymethylene on the oxygen gas introduction rate, pressure or plasma output obtained when oxygen gas was introduced.
Figure 3B:
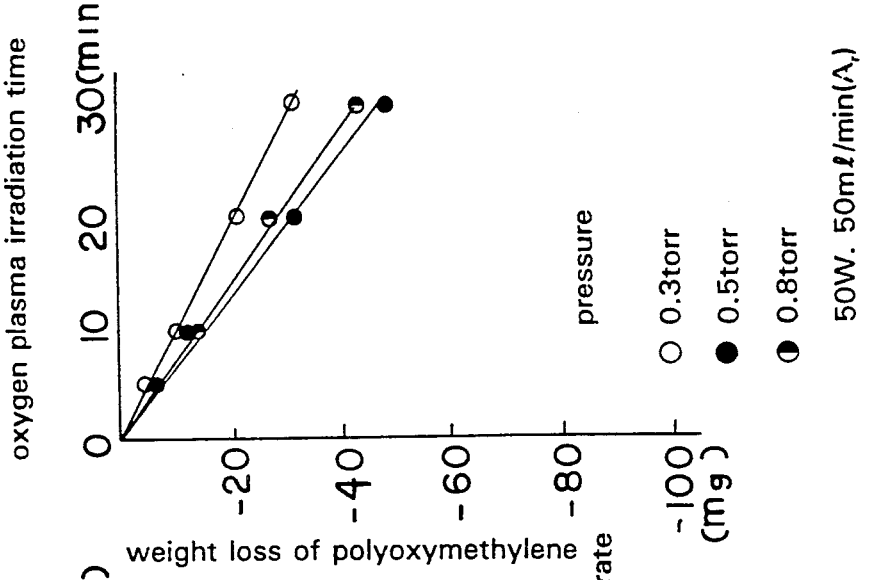
Figure 3A:
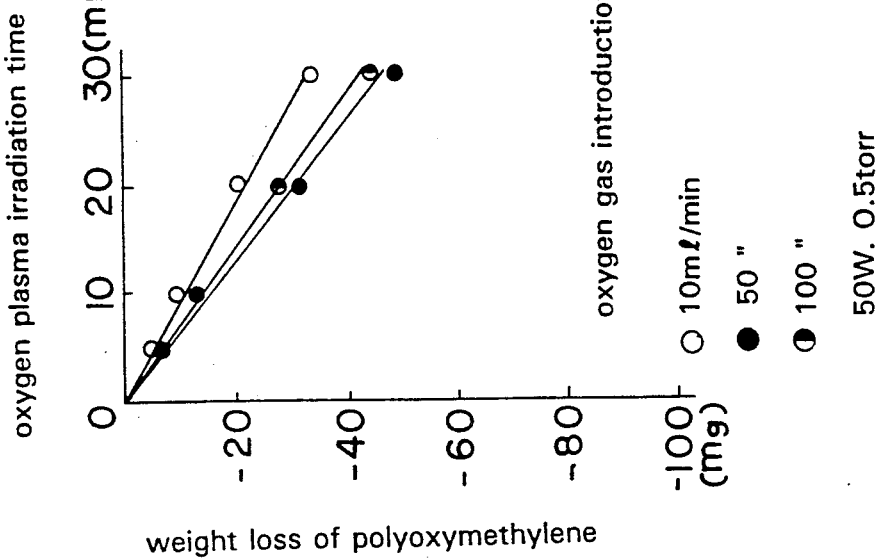

For example, a plasma was generated by the inductive coupling system wherein a 13.56-MHz high-frequency generation power supply device (0 to 200 W) as shown in FIG. 1 was used in Example 1 given below. In FIG. 1, reference numeral 1 is a gas cylinder, 2 is a flow meter, 3 is a high-frequency generation power supply, 4 is a matching network, 5 is a high-frequency coil, 6 is a trap, 7 is a pressure gauge and 8 is a reaction apparatus. FIG. 2 is an enlarged view of the reaction apparatus 8. In FIG. 2, reference numeral 9 is a tablet, 10 is a glass sample holder and 11 is an O-ring. A preferred effective output is 50 to 100 W, and a preferred gas flow rate for plasma formation is about 50 ml/min under 0.5 Torr. Both the pressure and flow rate are employed as the parameters so that the sample can be efficiently irradiated with the plasma. Since the purpose can be attained merely by irradiating the sample surface with the plasma, a reaction apparatus of any shape can be used. In Examples 1 and 2, a glass sample holder 10 having three thin legs was used so that both surfaces of the tablet could be uniformly irradiated with the plasma. A tablet 9 was placed on the sample holder 10. Two or more tablet samples can be irradiated simultaneously when a larger reaction apparatus is used. When the sample is in another form such as granules, a large amount of the sample can be efficiently irradiated with the plasma by using an inversion plasma irradiation reaction apparatus.

The multi-layer solid preparation of the present invention comprises a core substance in the form of a tablet or granule containing an active medicinal ingredient and one or more layers formed thereon, wherein the outermost layer comprises a plasma-decomposable polymer and a plasma-crosslinkable polymer and has been irradiated with a plasma. In Examples 1 and 2 given below, a tablet containing theophylline is used as the core and it is coated with a layer comprising a plasma-decomposable polymer and a plasma-crosslinkable polymer. This double-layer tablet is formed by the direct tableting method. The surface of the layer is irradiated with a plasma to obtain the multi-layer solid preparation of the present invention.

It is desirable to conduct a preliminary test for finding out the optimum conditions for the plasma irradiation. The preliminary test is, for example, a weight loss test in which the weight loss due to the plasma decomposition reaction is determined according to the irradiation conditions.

Examples

The following Examples will further illustrate the present invention.

Example 1

Polyoxymethylene and polystyrene are typical plasma-decomposable polymer and plasma-crosslinkable polymer, respectively. Double-layer tablets containing theophylline and having the outer layer comprising these polymers were produced.

Purification of commercially available polystyrene 5 g of commercially available polystyrene was dissolved in 60 ml of purified benzene and then reprecipitated in 45 ml of methanol. After the removal of the supernatant liquid, the polystyrene was again dissolved in 60 ml of purified benzene, reprecipitated in 1.25 l of methanol and thoroughly stirred. It was filtered and dried at 60° C. under reduced pressure. Then the product was pulverized with a ball mill and sieved to obtain the product of an intended particle diameter.

Synthesis of polyoxymethylene

A condenser, a nitrogen-introducing tube and a thermometer were attached to a 100-ml three-necked flask. Air in the flask was replaced with nitrogen. 42 g of trioxane and 18 ml of dry cyclohexane were placed therein and heated to 55° C. while introducing nitrogen thereinto to obtain a solution. A solution of 0.9 μl of boron trifluoride diethyl etherate catalyst in cyclohexane was added thereto. The polymerization was completed in several hours. The product was poured into 100 ml of acetone containing 0.3 ml of tributylamine, thoroughly stirred and then filtered. The filter cake was thoroughly washed with acetone. After air-drying at 60° C., the product was pulverized in a motor and sieved to obtain the product of an intended particle diameter.

Samples

Production of theophylline-containing double-layer tablets polyoxymethylene (passed through a 60 to 80 mesh screen)

polystyrene (passed through a 200 mesh screen), and theophylline (passed through a 32 mesh screen)

Theophylline (100 mg) was molded into a disk-shaped capsule having a diameter of 10 mm by applying a tableting pressure of 40 kg/cm$^2$ for 10 sec with a 10 mm-diameter KBr tableting machine mfd. by Shimadzu Corp. The theophylline tablet was placed at the center of a powdery mixture (80 mg) of polystyrene and polyoxymethylene in a ratio of 1:1. They were molded into a disk-shaped double-layer tablet having a diameter of 13 mm by applying a tableting pressure of 200 kg/cm$^2$ for 30 sec with a 13 mm-diameter KBr tableting machine mfd. by Shimadzu Corp.

Plasma irradiation

A plasma reaction apparatus shown in FIG. 1 was used for the plasma irradiation. The tablet 9 was placed on the sample holder 10 having three thin legs so as to uniformly irradiate both surfaces of the tablet with the plasma as shown in FIG. 2.

After irradiation with an 80-W plasma for 200 min, a tablet coated with crosslinked polystyrene was obtained.

Example 2

Double-layer tablets were produced in the same manner as that of Example 1 except that polystyrene was replaced with polylactic acid which is a polymer decomposable in vivo. The tablets were irradiated with a 6-W plasma for two hours to obtain those coated with crosslinked polylactic acid.

Effect of the Invention

The following Experimental Examples will illustrate the effect of the present invention:

Experimental Example 1

1) Influence of introduced gas on the weight loss of polyoxymethylene or polystyrene The following experiments were conducted with 100 mg disk-shaped tablets of polyoxymethylene or polystyrene having a diameter of 13 mm.

The plasma irradiation was conducted with the plasma reaction apparatus shown in FIG. 1.

Figure 4C:
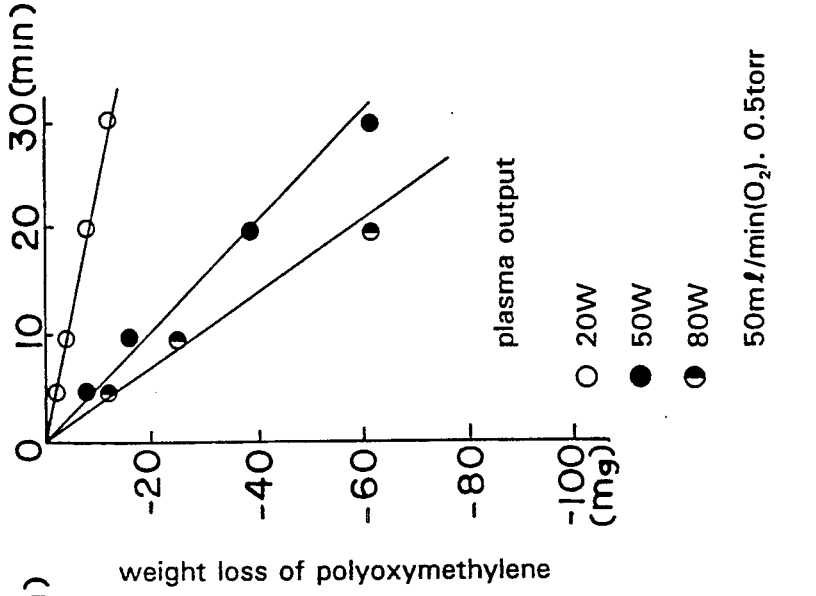
FIGS. 4(a), 4(b) and 4(c) show the results of the experiments on the dependency of the rate of weight loss of polyoxymethylene on the argon gas introduction rate, pressure or plasma output obtained when argon gas was introduced.
Figure 4B:
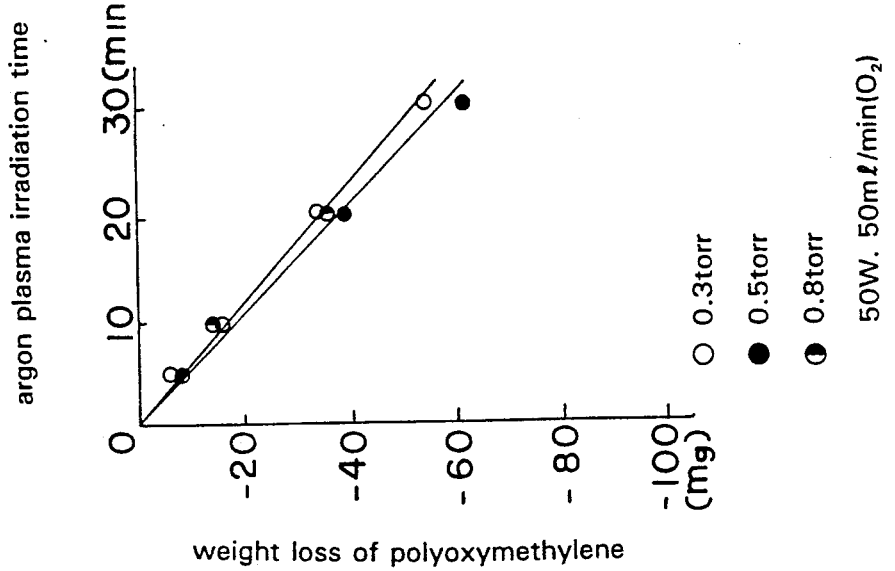
Figure 4A:
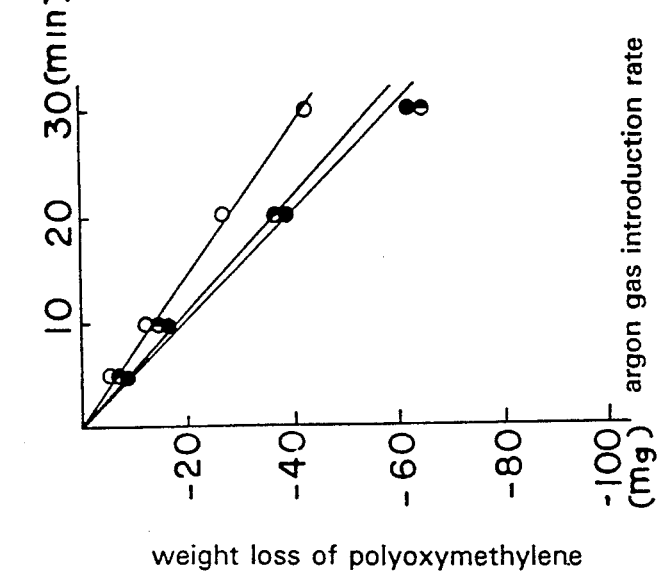
Figure 5C:
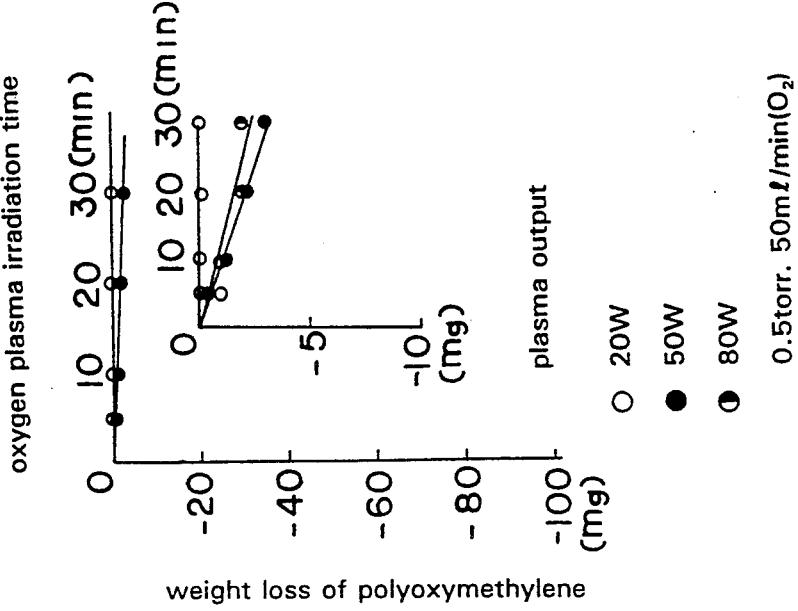
FIGS. 5(a), 5(b) and 5(c) show the results of the experiments on the dependency of the rate of weight loss of polystyrene on the oxygen gas introduction rate, pressure or plasma output obtained when oxygen gas was introduced.
Figure 5B:
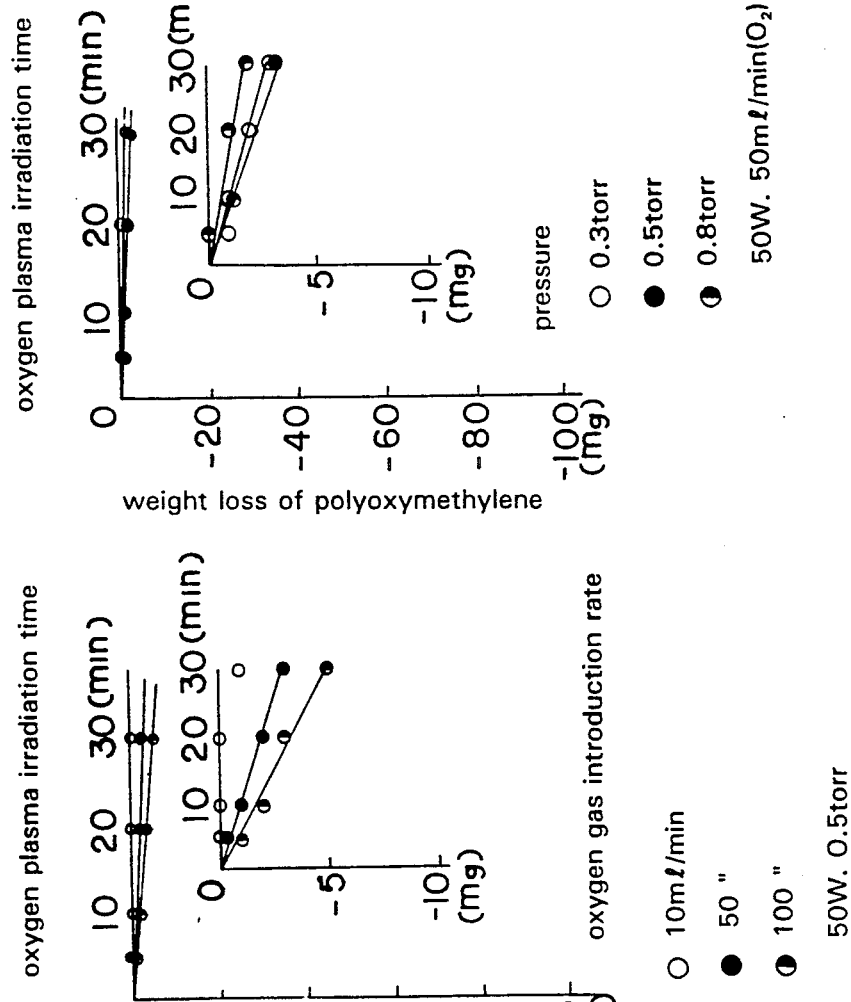
Figure 5A:
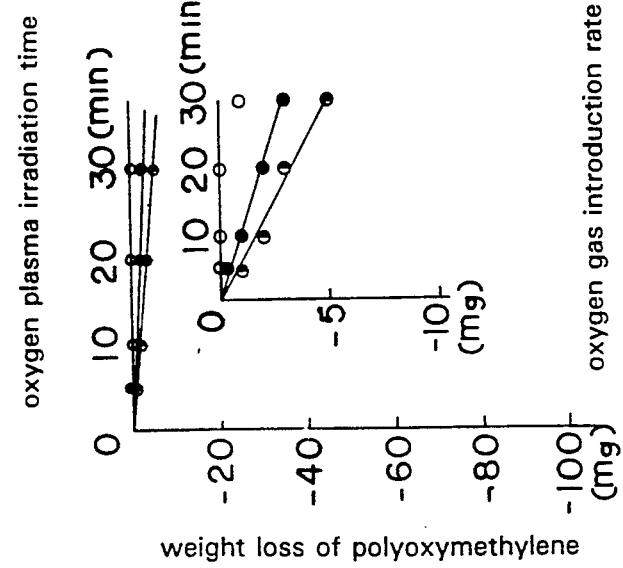

The results of the experiments on the dependency of the weight loss rate of polyoxymethylene or polystyrene on the introduction rate of oxygen or argon gas, pressure and plasma output are shown in FIGS. 3(a) to (c) through 6(a) to (c) FIGS. 3(a)-3(c) show the results of the experiments on dependency of the weight loss rate of polyoxymethylene on the oxygen gas introduction rate, pressure or plasma output obtained when oxygen gas was introduced. FIGS. 4(a)-4(c) show the results of the experiments on dependency of the weight loss rate of polyoxymethylene on argon gas introduction rate, pressure or plasma output obtained when argon gas was introduced. FIGS. 5(a)-5(c) show the results of the experiments on dependency of the weight loss rate of polystyrene on oxygen gas introduction rate, pressure or plasma output obtained when oxygen gas was introduced. FIGS. 6(a)-6(c) show the results of the experiments on the dependency of the weight loss rate of polystyrene on argon gas introduction rate, pressure or plasma output obtained when argon gas was introduced. FIGS. 3(a) through 6(a) indicate the relationship between the gas introduction rate and the weight loss rate, FIGS. 3(b) through 6(b) indicate the relationship between the pressure and the weight loss rate, and FIGS. 3(c) through 6(c) indicate the relationship between the plasma output and weight loss rate.

It is apparent from the results shown in FIGS. 3(a) to (c) through 6(a) to (c) that in the polyoxymethylene tablets, the plasma output exerted the greatest influence on the weight loss rate and that when an oxygen plasma was used, the weight loss rate was higher than that obtained when argon plasma was used by 30 to 40%. When the plasma irradiation conditions comprised an oxygen gas introduction rate of 50 ml/min, a pressure of 0.5 Torr and a plasma output of 50 W, a 100-mg polyoxymethylene tablet completely disappeared in one-hour plasma irradiation. On the contrary, the weight loss rate of the polystyrene tablet was only slight irrespective of the plasma irradiation conditions. This fact indicated that a high plasma output is desirable, since it increases the difference in the weight loss rate.

2) Dissolution Tests

Dissolution tests were conducted with double-layer tablets comprising a theophylline nucleus coated with a combination of polyoxymethylene and polystyrene produced in Example 1. The test methods were as given below.

Method

The dissolution test was conducted according to the rotating basket method described in the Japanese Pharmacopoeia. The dissolution tester was TR-5S3 made according to U.S.P. (NF) Standard by Toyama Sangyo K.K. The quantitative determination of eluted theophylline was conducted according to the absorbance measurement method described in the Japanese Pharmacopoeia.

Results (1) Relationship between oxygen plasma irradiation time and theophylline dissolution rate:

A double-layer tablet consisting of 100 mg of a theophilline core and a layer of 80 mg of a powdery mixture of 60 to 80-mesh polyoxymethylene and 200-mesh polystyrene in a ratio of 1:1 formed outside the core was irradiated with a plasma under conditions comprising a plasma output of 80 W, a pressure of 0.5 Torr and an oxygen gas flow rate of 50 ml/min for 0 to 30 min. The theophylline dissolution rate of each of the tablets thus obtained was determined. The results are shown in FIG. 7.

It is apparent from FIG. 7 that although theophylline was not eluted before the plasma irradiation and until 5 min after the initiation of the irradiation, the dissolution (rate) was increased thereafter with the plasma irradiation time. It is supposed from the weight loss of the tablet that by the plasma irradiation, the polyoxymethylene particles are decomposed and scattered from the outer layer, the polystyrene particles are made dense by the crosslinking reaction and pores, gaps and voids are formed in between the polystyrene particles. In FIG. 7, a comparatively good linearity is recognized up to a dissolution rate of around 80%, clearly suggesting zero-order release. However, when the plasma irradiation time was 30 min, theophylline is eluted quite rapidly (the dissolution is completed in about 2 h) and theophylline is partially decomposed. Thus the dissolution rate of theophylline does not exceed about 80% in this case.

(2) Relationship between oxygen plasma irradiation output and theophylline dissolution rate:

A theophylline-containing double-layer tablet consisting of 100 mg of a theophylline core and a layer of 80 mg of a powdery mixture of 60 to 80-mesh polyoxymethylene (POM) and 200-mesh polystyrene (PST) in a weight ratio of 1:1 formed outside the core was irradiated with a plasma under conditions comprising a plasma output of 20 to 80 W, a pressure of 0.5 Torr and an oxygen gas flow rate of 50 ml/min for 20 min. The theophylline dissolution rate of each of the tablets thus obtained was determined. The results are shown in FIG. 8.

With reference to the results of the weight loss test of POM tablets (FIGS. 3(a) to (c) to 6(a) to (c), the plasma irradiation output exerts a great influence on the weight loss of the tablets as described above. Also the dissolution test results of theophylline indicated that the dissolution surely depends on the plasma irradiation output as shown in FIG. 8. Namely, it will be understood that when the double-layer tablets produced under the above-described conditions are irradiated with a plasma of less than 50 W, the dissolution thereof is quite slight and, therefore, an output of about 50 to 80 W is preferred. This fact indicates that by suitably selecting the plasma irradiation output, the production of the multilayer grains having dissolution properties suitable for the purpose is made possible.

(3) Relationship between the ratio of the total weight of the polymers forming the outer layer to the active ingredient (theophylline) and theophylline dissolution rate:

A theophylline-containing double-layer tablet consisting of 100 mg of a theophylline core and an outer layer comprising 60 to 100 mg of a powdery mixture of 60 to 80-mesh polyoxymethylene (POM) and 200-mesh polystyrene (PST) in a weight ratio of 1:1 was irradiated with a plasma under conditions comprising a plasma output of 80 W, a pressure of 0.5 Torr and an oxygen gas flow rate of 50 ml/min for 20 min. The theophylline dissolution rate of each of the tablets thus obtained was determined. The results are shown in FIG. 9.

It will be apparent from FIG. 9 that when the total weight of the outer layer polymers was 60 mg for 100 mg of theophylline and the plasma irradiation time was 20 min, the dissolution of theophylline was extremely rapid (it was completed in about 3 h), theophylline was partially decomposed and even after the completion of the dissolution, a 100% elution rate could not be obtained but the rate was only around 80%. Thus, under these plasma irradiation conditions, 80 to 100 mg of the outer layer polymers are preferred for 100 mg of theophylline. By selecting the total weight of the outer layer polymers relative to the active ingredient (theophylline) within this range, the release pattern can be regulated.

(4) Relationship between the weight ratio of polymers forming the outer layer and dissolution rate of theophylline:

A theophylline-containing double-layer tablet consisting of 100 mg of a theophylline core and an outer layer comprising 80 mg of a powdery mixture of 60 to 80 -mesh polyoxymethylene (POM) and 200-mesh polystyrene (PST) in a weight ratio varying from 3:1 to 1:3 was irradiated with a plasma under conditions comprising a plasma output of 80 W, a pressure of 0.5 Torr and an oxygen gas flow rate of 50 ml/min for 20 min. The theophylline dissolution rate of each of the tablets thus obtained was determined. The results are shown in FIG. 10.

Figure 10:
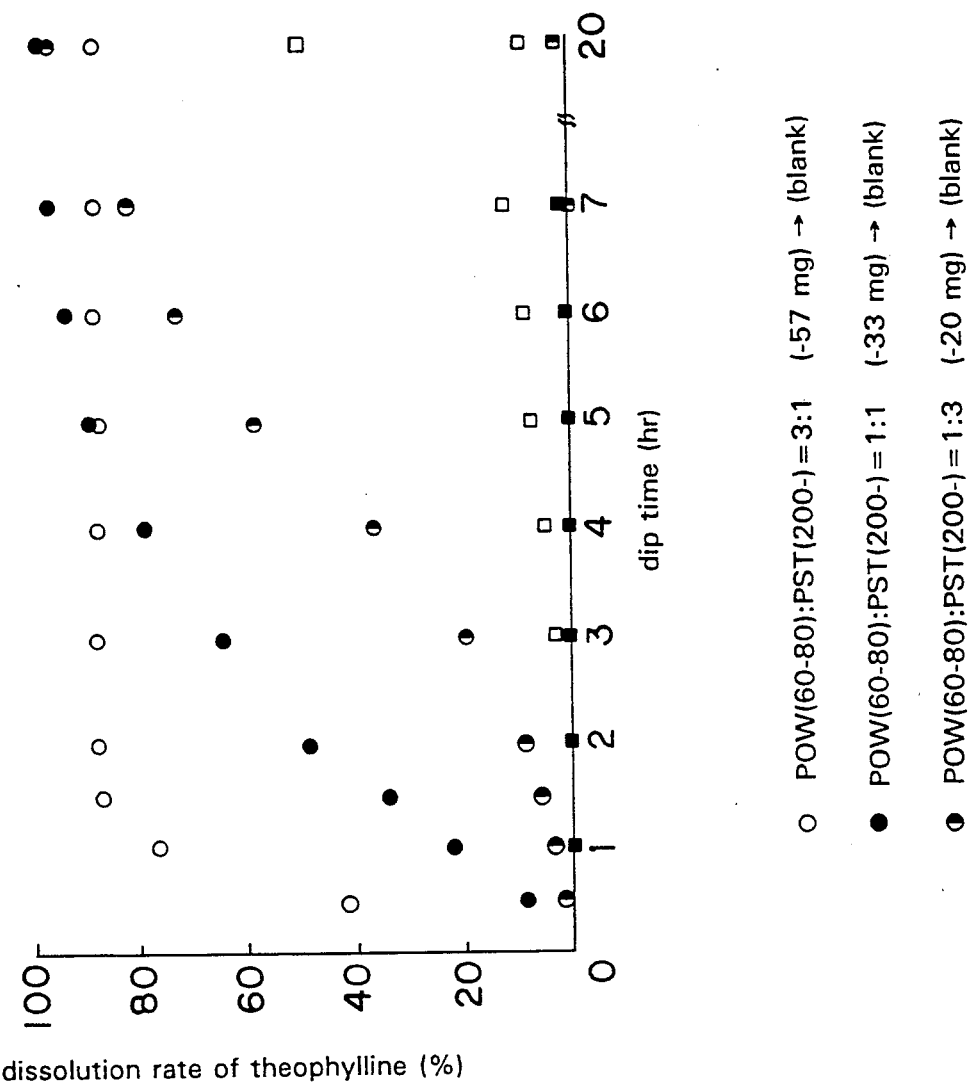
FIG. 10 shows the relationship between the weight ratio of the polymers forming the outer layer and dissolution rate of theophylline.

It will be apparent from FIG. 10 that when the weight ratio of POM to PST in the outer layer was 3:1 under these irradiation conditions, the dissolution of theophylline was extremely rapid (it was completed in about 2 h), theophylline was partially decomposed and even after the completion of the dissolution, a 100% dissolution rate could not be obtained but the rate was only about 90%. In the dissolution test of the same double-layer tablet having a weight ratio of POM to PST of 3:1 but which was not subjected to the plasma irradiation (blank), the dissolution of theophylline was caused, since POM which was the main component of the outermost layer was a hydrophilic polymer. On the contrary, when the weight ratio of POM to PST in the outer layer was 1:3, the dissolution of theophylline was extremely slow and a lag time was caused and, therefore, the dissolution pattern was of a solenoid type. Accordingly, the weight ratio of POM to PST in the outer layer is preferably about 1:1 under these plasma irradiation conditions. In this case, the zero-order release is substantially possible up to a dissolution rate of about 80%. It was thus suggested that the release pattern can be regulated also by selecting the ratio of the plasma-decomposable polymer to the plasma-crosslinkable polymer in the outer layer.

(5) Relationship between combination of polymers having various particle diameters in the outer layer and dissolution rate of theophylline:

The dissolution of theophylline from theophylline-containing double-layer tablets comprising polyoxymethylene (POM) and polystyrene (PST) having various particle diameters was examined while the polymer ratio in the outer layer and the total weight of them were fixed at 1:1 and 80 mg, respectively, and the plasma irradiation time was fixed at 20 min.

In the test, polyoxymethylene and polystyrene having particle diameters of 60 to 80 mesh, 100 to 140 mesh or 200 mesh or larger were used. Theophylline-containing double-layer tablets each consisting of 100 mg of a theophylline core and an outer layer comprising 80 mg of a powdery mixture of polyoxymethylene and polystyrene in a ratio of 1:1 were irradiated with a plasma under conditions comprising a plasma output of 80 W, a pressure of 0.5 Torr and an oxygen gas flow rate of 50 ml/min for 20 min. The theophylline dissolution rate of each of the tablets thus obtained was determined. The results are shown in FIG. 11.

Figure 11:
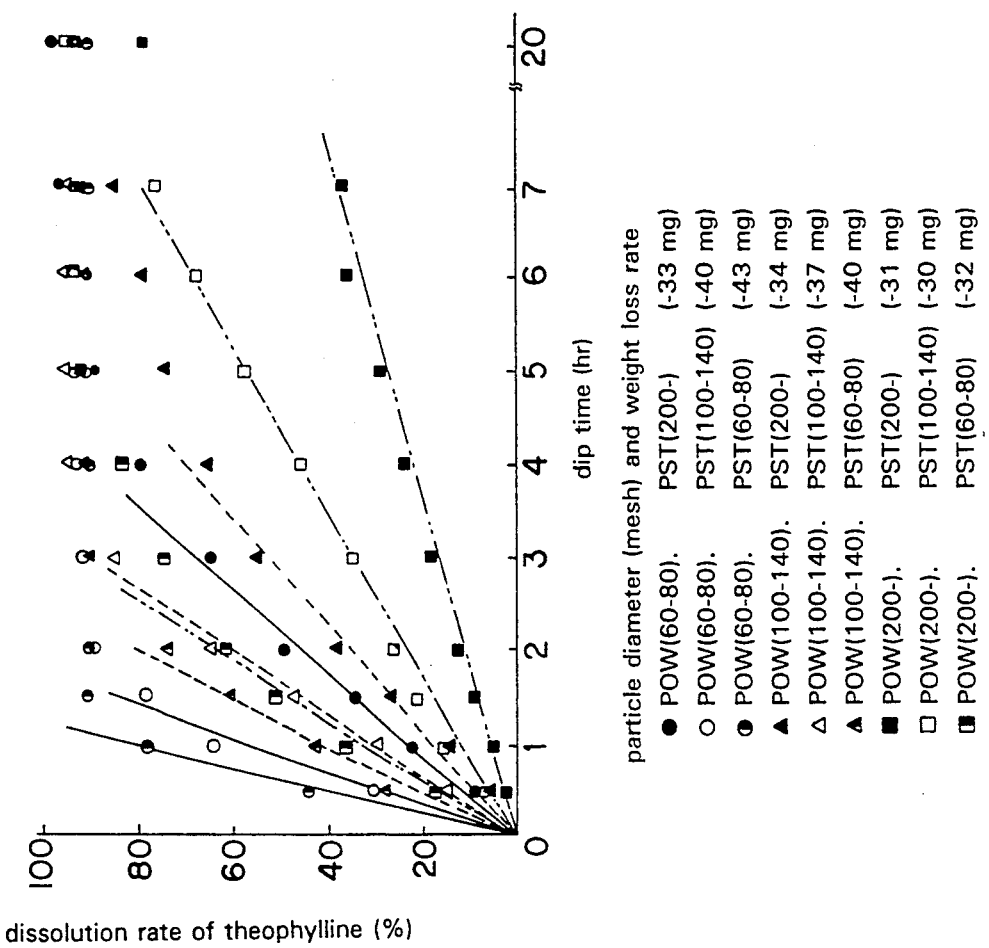
FIG. 11 shows the relationship between the combination of polymers having various particle diameters in the outer layer and dissolution rate of theophylline.

It is apparent from FIG. 11 that the larger the particle diameter of polyoxymethylene (POM) (plasma-decomposable polymer) or polystyrene (PST) (plasma-crosslinkable polymer), the higher the dissolution rate of theophylline. Namely, when the particle diameter of polystyrene (plasma-crosslinkable polymer) was constant, the dissolution rate was increased as the particle diameter of polyoxymethylene (plasma-decomposable polymer) was increased. Supposedly this is because the pores, gaps and voids formed in between the polystyrene particles are enlarged after the polyoxymethylene particles in the outer layer are decomposed or scattered upon the irradiation of the plasma as described above. When the particle diameter of polyoxymethylene is constant, the dissolution is increased as the particle diameter of polystyrene is increased. Supposedly this is because the gaps formed in between the polystyrene particles after the decomposition and scattering of the polyoxymethylene particles in the outer layer are enlarged as the particle diameter of polystyrene is increased. In other words, supposedly the crosslinking reaction induced by the plasma irradiation is inhibited, since the specific surface area of polystyrene is reduced. This fact clearly suggests that multi-layer granules having a desired elution rate can be produced by selecting either the particle diameters of the plasma-decomposable polymer and plasma-crosslinkable polymer constituting the outer layer or by selecting the particle diameter ratio of the former to the latter.

Summary of the results

The results of the dissolution tests of theophylline suggested that the theophylline release pattern can be varied as desired by selecting the plasma irradiation conditions (irradiation time and irradiation output) when the double-layer tablet production conditions are constant as shown in the relationship (1) and (2) or by selecting the conditions of formation of the outermost layer comprising the two polymers of the double-layer tablet (weight of each polymer forming the outer layer, ratio of them, and particle diameters of them) when the plasma irradiation conditions are constant as shown in the relationships (3), (4) and (5). Namely, it is possible to design sustained release preparations over a wide range.

Experimental Example 2

1) Weight loss of polyoxymethylene, polystyrene or polylactic acid upon plasma irradiation:

100 mg disk-type tablets (diameter: 13 mm) of polylactic acid, polyoxymethylene or polystyrene were used in the following experiments.

Oxygen plasma irradiation was conducted under conditions comprising an effective output of 6 W, an oxygen flow rate of 50 ml/min and a pressure of 0.5 Torr to determine the weight loss rate of polyoxymethylene, polystyrene or polylactic acid. The results are shown in FIG. 12.

Figure 12:
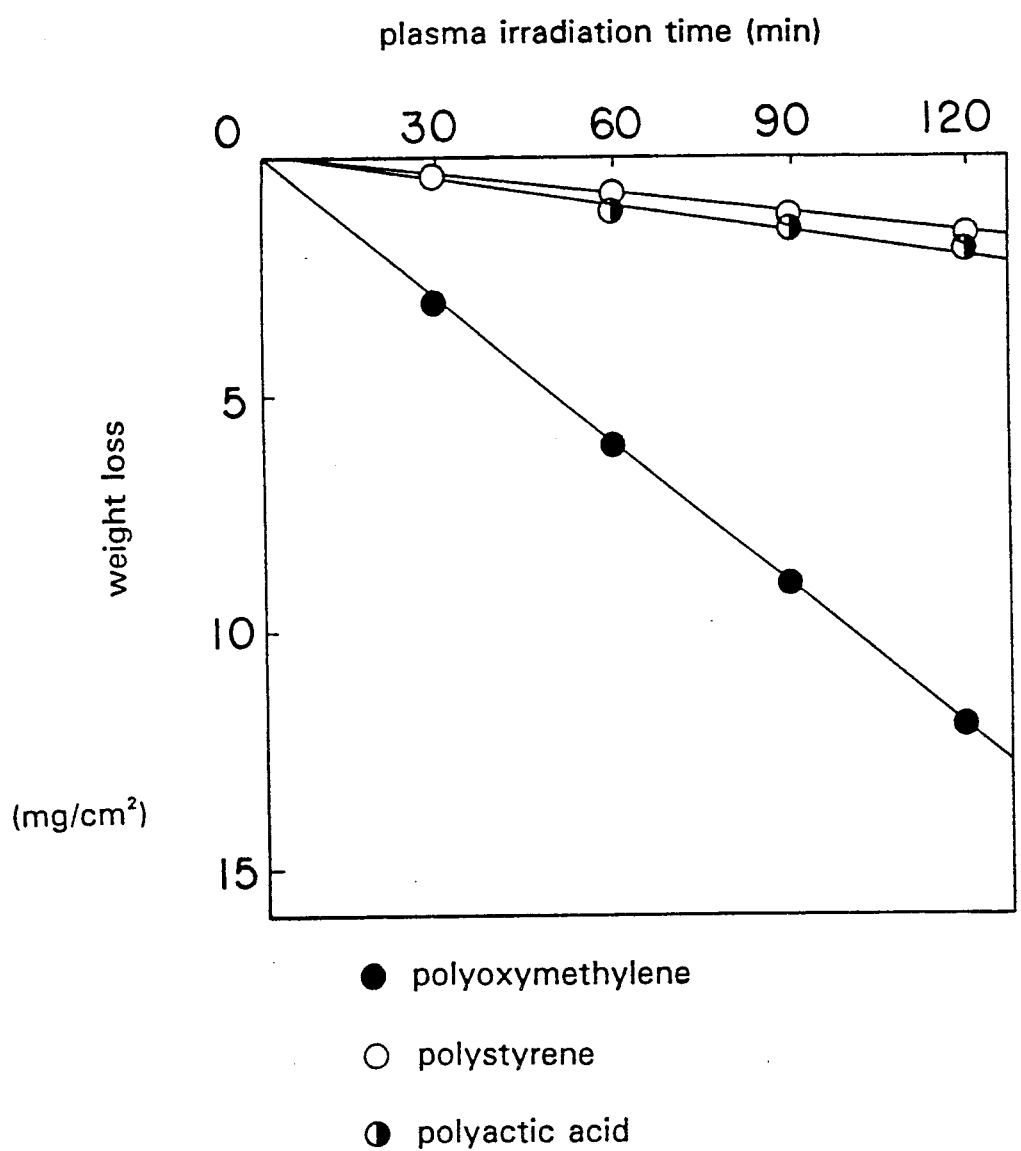
FIG. 12 shows the influence of oxygen plasma irradiation on the weight loss rate of polyoxymethylene or polyactic acid.

It is apparent from FIG. 12 that the weight loss rates were lower and the plasma irradiation times were longer than those of Experimental Example 1, since the output was lower than that of Experimental Example 1. However, the weight loss rate of polylactic acid was almost equal to that of polystyrene and far from that of polyoxymethylene.

2) Dissolution test:

The same double-layer tablets as those used in Example 2 which comprised a theophylline core and a combination of polyoxymethylene with polylactic acid as the outer layer were subjected to the tests described below.

Method

The dissolution test was conducted in the same manner as that of Experimental Example 1.

Results (1) Relationship between oxygen plasma irradiation time and theophylline dissolution rate:

A double-layer tablet consisting of 100 mg of a theophylline core and an outer layer of 80 mg of a powdery mixture of 60 to 80-mesh polyoxymehtylene and 100-mesh polylactic acid in a ratio of 1:3 was irradiated with a plasma output under conditions comprising a plasma output of 6 W, a pressure of 0.5 Torr and an oxygen gas flow rate of 50 ml/min for 1 to 3 h. The theophylline dissolution rate of each of the tablets thus obtained was determined. The results are shown in FIG. 13.

Figure 13:
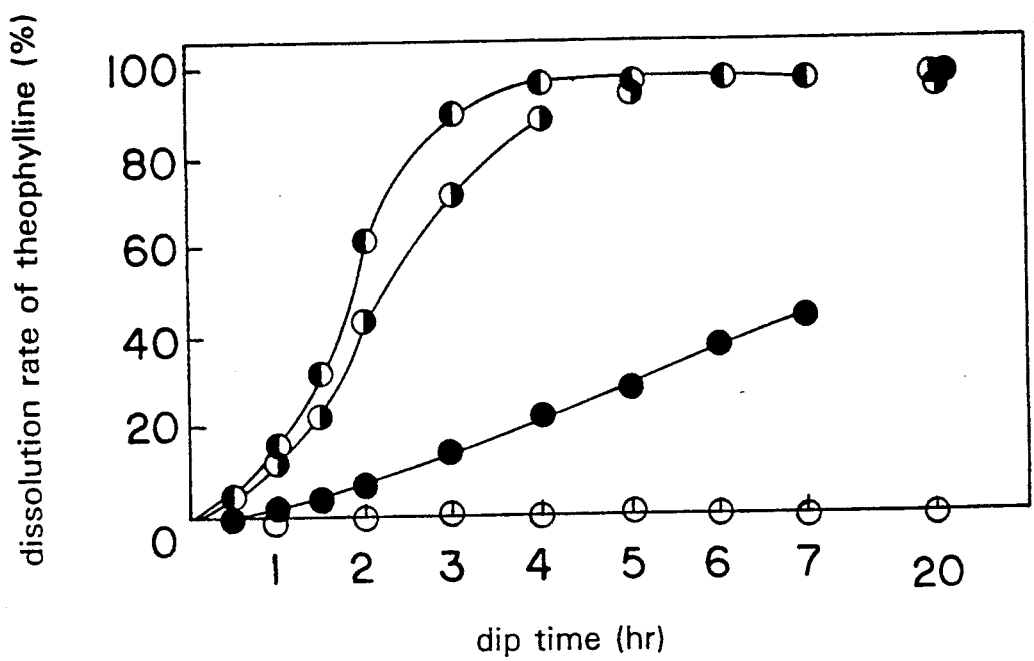
FIG. 13 shows the relationship between oxygen plasma irradiation time and dissolution rate of theophylline.

It is apparent from FIG. 13 that the dissolution (rate) was increased as the plasma irradiation time was prolonged. It is supposed from the weight loss of the tablet that by the plasma irradiation, the polyoxymethylene particles in the outer layer are decomposed and scattered, the polylactic acid particles are made dense by the crosslinking reaction and pores, gaps and voids are formed in between the polystyrene particles.

(2) Relationship between oxygen plasma irradiation output and theophylline dissolution rate:

A theophylline-containing double-layer tablet consisting of 100 mg of a theophylline core and an outer layer of 80 mg of a powdery mixture of 60 to 80-mesh polyoxymethylene and 100-mesh polylactic acid in a weight ratio of 1:3 was irradiated with the plasma under comprising a pressure of 0.5 Torr, an oxygen gas flow rate of 50 ml/min, a plasma irradiation time of 2 h, and a plasma irradiation output of 4 to 8 W. The theophylline dissolution rate of each of the tablets thus obtained was determined. The results are shown in FIG. 14.

Figure 14:
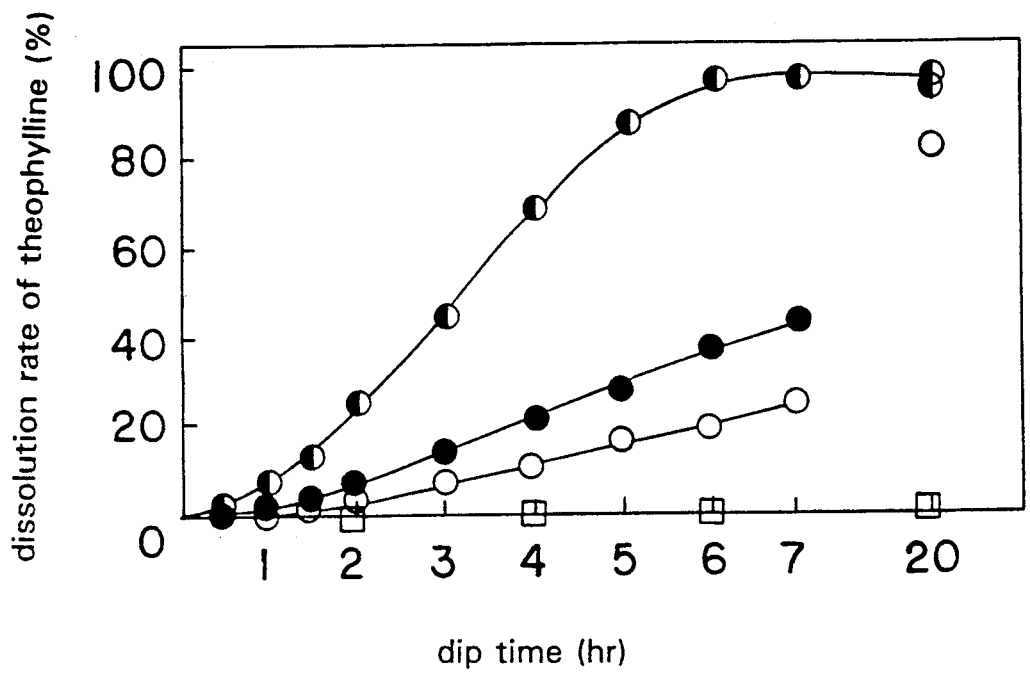
FIG. 14 shows the relationship between oxygen plasma irradiation output and dissolution rate of theophylline.

It is apparent from FIG. 14 that the dissolution significantly depends on the plasma irradiation output. This fact suggests that multi-layer tablets having a desired dissolution rate can be produced by suitably selecting the output.

(3) Relationship between the ratio of the total weight of the polymers forming the outer layer to the active ingredient (theophylline) and theophylline dissolution rate:

A theophylline-containing double-layer tablet consisting of 100 mg of a theophylline core and outer layer comprising 60 to 100 mg of a powdery mixture of 60 to 80-mesh polyoxymethylene and 100-mesh polylactic acid in a weight ratio of 1:3 was irradiated with the plasma under conditions comprising a plasma irradiation output of 6 W, a pressure of 0.5 Torr and an oxygen flow rate of 50 ml/min for 2 h. The theophylline dissolution rate of each of the tablets thus obtained was determined. The results are shown in FIG. 15.

Figure 15:
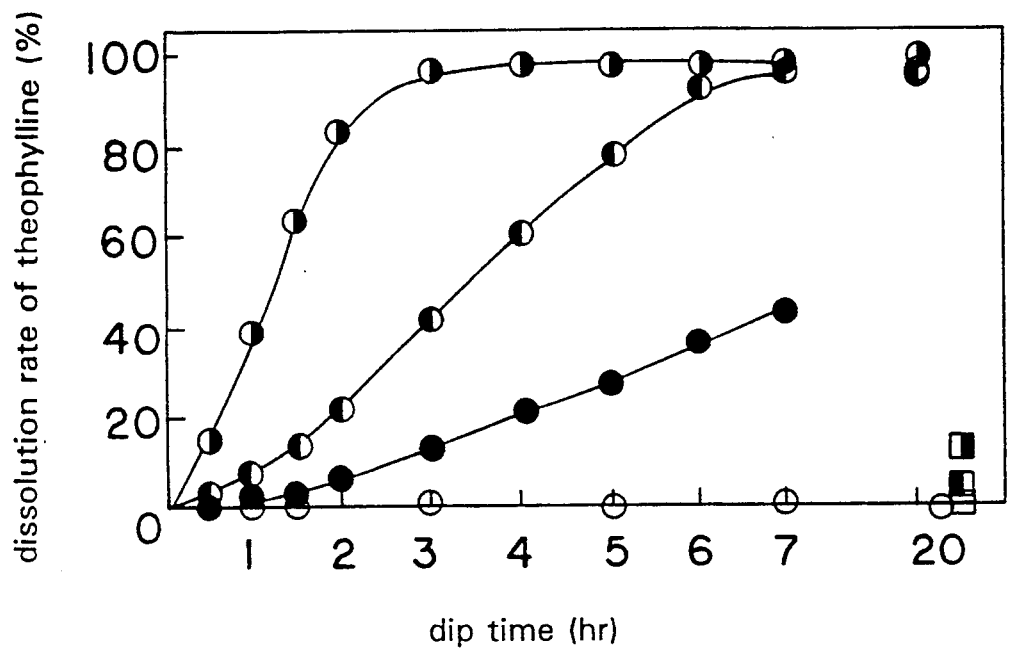
FIG. 15 shows the relationship between the ratio of the total weight of the polymers forming the outer layer to the active ingredient (theophylline) and dissolution rate of theophylline.

It is apparent from FIG. 15 that when the total weight of the outer layer polymers was 60 mg for 100 mg of theophylline and the plasma irradiation time was 2 h, the dissolution rate of theophylline was high (it was completed in about 3 h) and that when the total weight of these polymers was 100 mg, theophylline was scarcely eluted. Thus, under these plasma irradiation conditions, 60 to 80 mg of the polymers are preferred for 100 mg of theophylline. By selecting the total weight of the outer layer polymers relative to the active ingredient (theophylline) within this range, the release pattern can be regulated.

(4) Relationship between the weight ratio of polymers forming the outer layer and dissolution rate of theophylline:

A theophylline-containing double-layer tablet consisting of 100 mg of a theophylline core and an outer layer comprising 80 mg of a powdery mixture of 60 to 80-mesh polyoxymethylene (POM) and 100-mesh polylactic acid (PLA) in a weight ratio varying from 3:1 to 1:3 was irradiated with a plasma under conditions comprising a plasma irradiation output of 6 W, a pressure of 0.5 Torr and an oxygen gas flow rate of 50 ml/min for 2 h. The theophylline dissolution rate of each of the tablets thus obtained was determined. The results are shown in FIG. 16.

Figure 16:
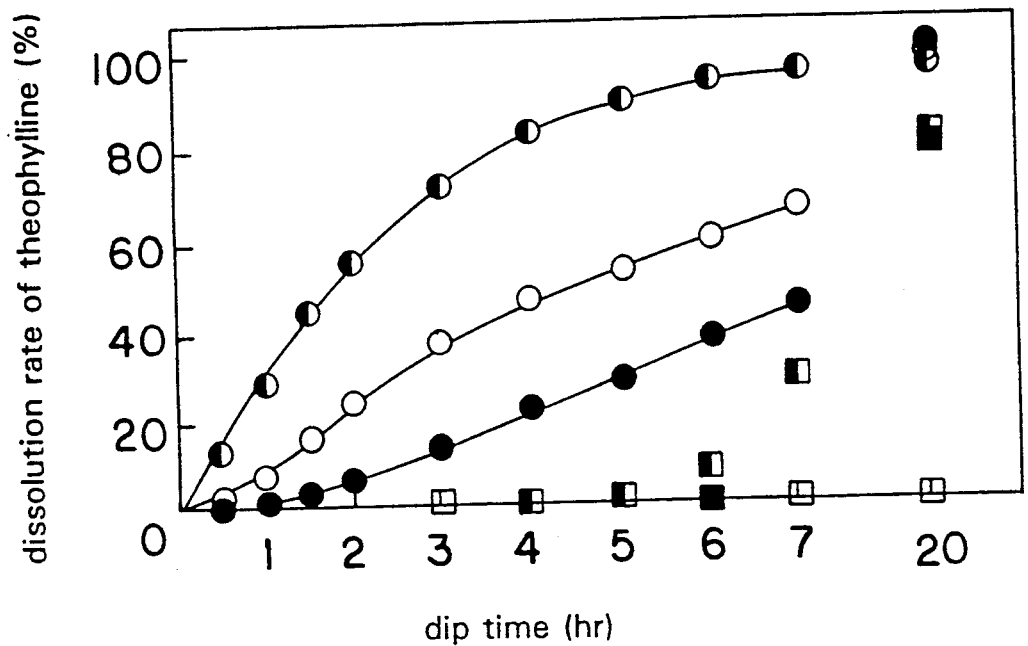
FIG. 16 shows the relationship between the weight ratio of the polymers forming the outer layer and dissolution rate of theophylline.

It will be apparent from FIG. 16 that the release pattern can be controlled also by selecting the ratio of the plasma-decomposable polymer to the plasma-crosslinkable polymer forming the outer layer.

(5) Relationship between combination of polymers having various particle diameters in the outer layer and dissolution rate of theophylline:

The dissolution of theophylline from theophylline-containing double-layer tablets comprising polyoxymethylene (POM) and polylactic acid (PLA) having various particle diameters were examined while the polymer ratio in the outer layer and the total weight of them were fixed at 1:3 and 80 mg, respectively, and the plasma irradiation time was fixed at 2.5 h.

In the test, polyoxymethylene having particle diameters of 60 to 80 mesh, 100 to 140 mesh or 200 mesh or larger and polylactic acid having a particle diameter of 100 mesh or larger were used. Double-layer tablets each consisting of 100 mg of a theophylline core and an outer layer comprising 80 mg of a powdery mixture of polyoxymethylene and polylactic acid in a ratio of 1:3 were irradiated with the plasma under conditions comprising a plasma output of 6 W, a pressure of 0.5 Torr and an oxygen gas flow rate of 50 ml/min for 2.5 h. The theophylline dissolution rate of each of the tablets thus obtained was determined. The results are shown in FIG. 17.

It is apparent from FIG. 17 that the larger the particle diameter of polyoxymethylene (POM) (plasma-decomposable polymer), the higher the elution rate of theophylline. Namely, when the particle diameter of polylactic acid (plasma-crosslinkable polymer) was constant, the dissolution rate was increased as the particle diameter of polyoxymethylene (plasma-decomposable polymer) was increased. Supposedly this is because the pores, gaps and voids formed in between the polylactic acid particles are enlarged after the polyoxymethylene particles in the outer layer are decomposed or scattered upon the irradiation of the plasma as described above. This fact clearly suggests that multi-layer tablets having a desired dissolution rate can be produced also by selecting the particle diameter of the plasma-decomposable polymer constituting the outer layer.

Summary of the results

It is apparent from the results that the dissolution rate of theophylline can be controlled under various conditions even when polystyrene is replaced with polylactic acid. When the plasma irradiation output is low as in this experiment, polylactic acid is not decomposed. Since polylactic acid is a polymer decomposable in vivo, this method is useful for the production of implantable DDS preparations.

We claim:

1. A multi-layer solid preparation comprising a core, an outer layer covering said core, said outer layer comprising a mixture of a plasma-decomposable polymer and a plasma-crosslinkable polymer, which mixture has been irradiated with a plasma of a non-organic gas effective to decompose said plasma-decomposable polymer and to crosslink said plasma-crosslinkable polymer.

2. A multi-layer solid preparation according to claim 1 wherein the plasma-decomposable polymer si selected from the group consisting of polyisobutylene, poly-α-methylstyrene, polymethacrylic acid, polymethyl methacrylate, polymethacrylamide, polyoxymethylene and polysaccharide.

3. A multi-layer solid preparation according to claim 1 wherein the plasma-crosslinkable polymer is selected from the group consisting of polypropylene, polystyrene, polyacrylic acid, polymethyl acrylate, polyacrylamide and polylactic acid.

4. A multi-layer solid preparation according to claim 1 wherein the plasma is selected from the group consisting of argon plasma, helium plasma, oxygen plasma, nitrogen plasma, hydrogen plasma, air plasma and water plasma.

5. A process for producing a multi-layer solid preparation as set forth in claim 1, comprising coating a core with an outermost layer comprising a plasma-decomposable polymer and a plasma-crosslinkable polymer and then irradiating the outermost layer with a plasma of a non-organic gas effective to decompose said plasma-decomposable polymer and to crosslink said plasma-crosslinkable polymer.

6. A solid, prolonged action, dosage form for oral delivery of a drug to a patient, comprising: a core containing a therapeutically effective amount of the drug; an outermost layer covering said core, said outermost layer comprising a mixture of a first, plasma-decomposable polymer and a second, plasma-crosslinkable polymer, said dosage form having been irradiated by contacting same with a plasma of a non-organic gas containing an approximately equal number of positive ions and electrons, said irradiation being effective to cause formation of radicals on said polymers, the radicals on said second polymer causing cross-linking of said second polymer, said irradiation having been carried out for a period of time so that said outer layer comprises a mesh of said second polymer which has been crosslinked and which is effective for controlling diffusion and elution of the drug.

7. A dosage form as claimed in claim 6 in which said drug is theophylline.

8. A dosage form as claimed in claim 6 in which the weight ratio of said first polymer/said second polymer is from ⅓ to 3/1.

9. A dosage form as claimed in claim 6 in which said first polymer undergoes breakage of the main chain thereof and loss of weight when irradiated by said plasma, and said second polymer forms radicals of the same kind as the main chain of said second polymer when irradiated with said plasma and said radicals are effective to cause a surface crosslinkiing reaction.

10. A dosage form as claimed in claim 6 in which said first polymer is polyoxymethylene and said second polymer is polystyrene.

11. A dosage form as claimed in claim 6 in which said first polymer is polyoxymethylene and said second polymer is polylactic acid.

12. A process for preparing a solid, prolonged action, dosage form for oral delivery of a drug to a patient, comprising the steps of: coating a core containing a therapeutically effective amount of the drug with an outermost layer, said outermost layer comprising a mixture of a first, plasma-decomposable polymer and a second, plasma-crosslinkable polymer, contacting said outermost layer with a plasma of a non-organic gas containing an approximately equal number of positive ions and electrons, to irradiate said outermost layer and cause formation of radicals on said polymers, the radicals on said second polymer causing cross-linking of said second polymer, the irradiation being carried out for a period of time so that said outer layer comprises a mesh of said second polymer which has been crosslinked and which is effective for controlling diffusion and elution of the drug.

* * * * *

UNITED STATES PATENT AND TRADEMARK OFFICE
CERTIFICATE OF CORRECTION

PATENT NO. : 5,306,505
DATED : April 26, 1994
INVENTOR(S) : Masayuki KUZUYA et al It is certified that error appears in the above-identified patent and that said Letters Patent is hereby corrected as shown below:

Column 13, line 46; change "si" to ---is---.

Column 14, line 37; change "crosslinkiing" to ---crosslinking---.

Signed and Sealed this

Ninth Day of August, 1994

Attest:

BRUCE LEHMAN

Attesting Officer

Commissioner of Patents and Trademarks